United States Patent [19]

Yun et al.

[11] Patent Number: 5,777,207
[45] Date of Patent: Jul. 7, 1998

[54] GAS SENSOR AND METHOD FOR FABRICATING THE SAME

[75] Inventors: Dong Hyun Yun, Kyungki-do; Kyuchung Lee, Seoul; Chul Han Kwon, Keungki-do; Hyung-Ki Hong, Kyungki-do, all of Rep. of Korea

[73] Assignee: LG Electronics Inc., Seoul, Rep. of Korea

[21] Appl. No.: 728,757

[22] Filed: Oct. 11, 1996

[30] Foreign Application Priority Data

Nov. 27, 1995 [KR] Rep. of Korea ............... 43917/1995

[51] Int. Cl.$^6$ ............... G01N 27/12; H01L 7/00; H01L 29/66
[52] U.S. Cl. ............... 73/31.05; 73/23.34; 338/34; 422/83; 422/98; 427/101; 427/103
[58] Field of Search ............... 73/31.05, 31.06, 73/23.34; 338/34; 422/83, 90, 98; 427/101–103

[56] References Cited

U.S. PATENT DOCUMENTS

| | | | |
|---|---|---|---|
| 4,313,338 | 2/1982 | Abe et al. | 73/23 |
| 4,399,424 | 8/1983 | Rigby | 338/34 |
| 4,583,070 | 4/1986 | Okayama | 338/34 |
| 4,638,443 | 1/1987 | Kaneyasu et al. | 364/497 |
| 4,652,849 | 3/1987 | Matsuura et al. | 338/34 |
| 4,731,226 | 3/1988 | Takahata et al. | 422/98 |
| 4,822,465 | 4/1989 | Jones et al. | 204/192.1 |
| 4,885,929 | 12/1989 | Kasahara et al. | 73/23 |
| 4,911,892 | 3/1990 | Grace et al. | 422/94 |
| 5,296,196 | 3/1994 | Takeshima | 422/98 |
| 5,457,333 | 10/1995 | Fukui | 257/253 |

*Primary Examiner*—Hezron E. Williams
*Assistant Examiner*—J. David Wiggins
*Attorney, Agent, or Firm*—John P. White

[57] ABSTRACT

Air pollution gas sensor which efficiently detects smell from smoking, ordinary stinks such as TMA and CH3SH, smell of Kimchi, acetaldehyde, and etc. and also a method for fabricating the same is revealed and described including a substrate, a heater formed on said substrate, electrodes each formed on said substrate insulated from the heater, and a sensing layer formed of $SnO_2$, including $WO_3$ on said substrate including said electrodes, with the method for fabricating the gas sensor including the steps of forming the heater on the substrate, forming the electrodes on the substrate insulated from the heater, and forming a sensing layer of $SnO_2$ including $WO_3$ on the substrate including the electrodes.

3 Claims, 4 Drawing Sheets process for fabricating a gas sensor process for fabricating a sensing material

GAS SENSOR AND METHOD FOR FABRICATING THE SAME

BACKGROUND OF THE INVENTION

1. Field of the Invention

The present invention relates to a gas sensor and, more particularly, to a air pollution gas sensor which efficiently detects smell from smoking, ordinary stinks such as TMA and $CH_3SH$, smell of Kimchi, acetaldehyde, and etc. and a method for fabricating the same.

2. Discussion of the Related Art

In general, an air pollution gas sensor is operated through a series of processes in which, when reducing gases floating in the air are adsorbed on the surface of a sensing material of the air pollution gas sensor, the air pollution gas sensor causes oxidation/reduction reactions with exchange of electrons. That is, the reducing gases R couple with the oxygen ions ($O^-$) already adsorbed on the surface of the heated sensor to generate conduction electrons that change electrical conductivity as shown in the below formula.

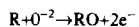

These reactions show great difference depending on reducing gases R, materials of the sensors (sensing materials), amounts and kinds of catalyst, operating temperature (heated temperature), and so on. Therefore, according to the gas to be detected, a sensing material of the sensor and a kind of a catalyst and its amount should be properly regulated. Besides, because the surface of the sensor needs to be appropriately heated, a heater has to be installed inside the sensor. In addition, cost, feasibility of mass production, and lifetime of the sensor should be taken into account.

Currently, the gas sensors are used in displays and deodoring devices in air cleaners,and air conditioners and the like for sensing and displaying air pollution levels, and conducting appropriate control over the pollution (i.e., for cleaning).

A conventional air pollution gas sensor will be discussed below with reference to FIG. 1.

As illustrated in FIG. 1, a conventional air pollution gas sensor for sensing an air pollution level includes a heater 2 fixed in a form of coils inside of a ceramic tube 1 for heating the sensor, electrodes 3-1, 3-2 having a lead line 4 connected thereto formed on an external wall of the ceramic tube 1, and a sensing layer 5 of $SnO_2$ mixed with a catalyst of precious metal, such as Pd or Pt on the external surface of the tube 1 between the electrodes 3-1, 3-2.

At first, the conventional air pollution gas sensor heats up the heater 2, maintains the heater at a predetermined elevated temperature for activating reaction of the sensing layer 5 with a gas to monitored be.

When a gas comes into contact with the surface of the heated sensing layer 5, electrons move between molecules of the gas to be detected and the surface of the sensing layer 5 to cause a change in electric conductivity, i.e., a different electrical resistance with subsequent change in an electric current flowing between both electrodes 3-1, 3-2, which is allowed to detect the presence of the gas.

FIG. 2 shows results of air pollution level measurement with a conventional air pollution gas sensor (a state of initial no gas exposure vs. a state of gas exposure). Referring to FIG. 2, from the fact that the resistances decrease as the concentrations of ethanol, hydrogen, and hydrocarbon increase, it is can be known that because the conventional air pollution gas sensor reacts with ethanol, hydrogen, and hydrocarbon, the conventional air pollution gas sensor mainly reacts with smells or gases containing the foregoing gases of the air pollution, constituents in everyday life.

As an typical example, as smoke from a cigarette undergoing the smoking process includes a trace of CO, $H_2$, HC, and etc., the conventional air pollution gas sensor is able to detect the smoke. Other than sensing cigarette smoking; the conventional air pollution gas sensor is mainly used to detect CO, $CH_4$, $C_4H_{10}$ which have nothing to do with air pollution levels or stink.

However, the conventional air pollution gas sensor has the following problems:

First, the conventional air pollution gas sensor is not relatively sensitive at detecting $CH_3CHO$ which is one of the common cigarette smoking smells $C_5H_{10}O_2$ which is a constituent of smells from sweat and foot, TMA|$CH_3|_3N$) and $CH_3SH$ which are stinks from rotten food, and Kimchi smell.

Second, since the structure of the conventional air pollution gas sensor is complicated and heater mounting and sensing layer coating are done manually one by one, the conventional air pollution gas sensor has a long fabrication process time, and is difficult to mass produce.

SUMMARY OF THE INVENTION

Accordingly, the present invention is directed to a air pollution gas sensor and a method for fabricating the same that substantially obviates one or more of the problems due to limitations and disadvantages of the related prior art.

An object of the present invention is to provide a air pollution gas sensor which detects smoke, stink from rotten food, sweat smell, and so on and a method for fabricating the same.

Another object of the present invention is to provide a air pollution gas sensor of which the structure is simplified for mass production and a method for fabricating the same.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof-as well as the appended drawings.

To achieve these and other advantages and in accordance with the purpose of the present invention, as embodied and broadly described, the air pollution gas sensor of the present invention includes a substrate, a heater formed on the substrate, electrodes each formed on the substrate and insulated from the heater, and a sensing layer formed of $SnO_2$ including $WO_3$ on the substrate including the electrodes.

In the other aspect of the present invention, there is provided a method for fabricating a air pollution gas sensor including the steps of providing a substrate, forming a heater on the substrate, "forming electrodes insulated from the heater," and forming a sensing layer of $SnO_2$ including $WO_3$ on the substrate including electrodes.

It is to be understood that both the foregoing general description and the following detailed description are exemplary and explanatory and are intended to provide further explanation of the invention as claimed.

BRIEF DESCRIPTION OF THE ATTACHED DRAWINGS

The accompanying drawings, which are included to provide a further understanding of the invention and are incor-

3 porated in and constitute a part of this specification, illustrate embodiments of the invention and together with the description serve to explain the principles of the drawings. In the drawings, FIG. 1 shows a structure of a conventional air pollution gas sensor;

DETAILED DESCRIPTION OF THE PREFERRED EMBODIMENTS

Reference will now be made in detail to the preferred embodiments of the present invention, examples of which are illustrated in the accompanying drawings.

Figure 1:
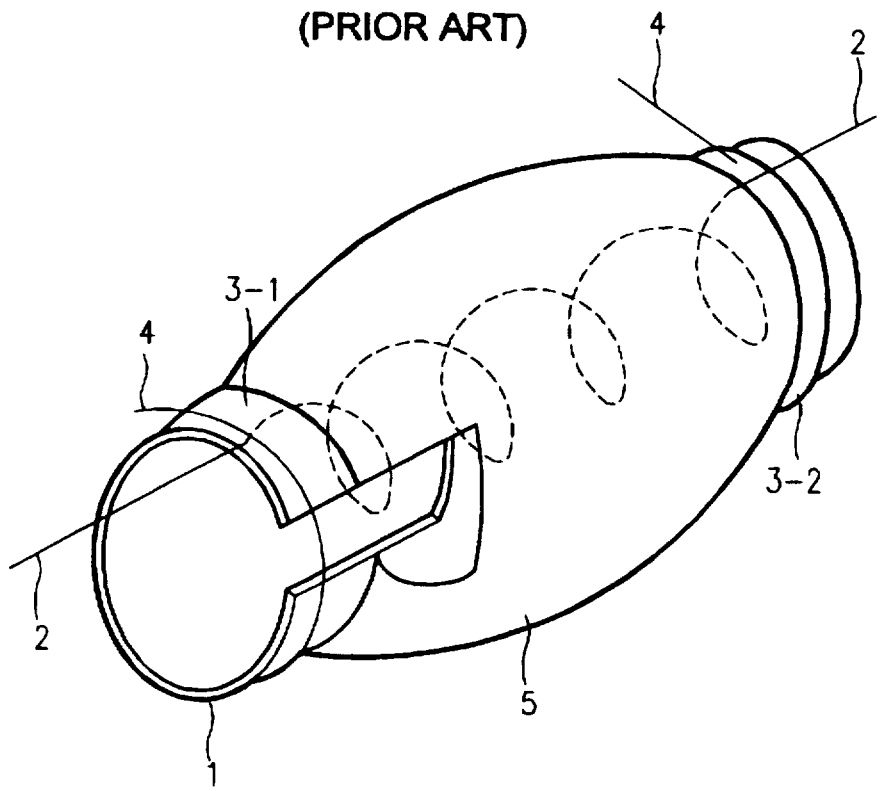
Figure 2:
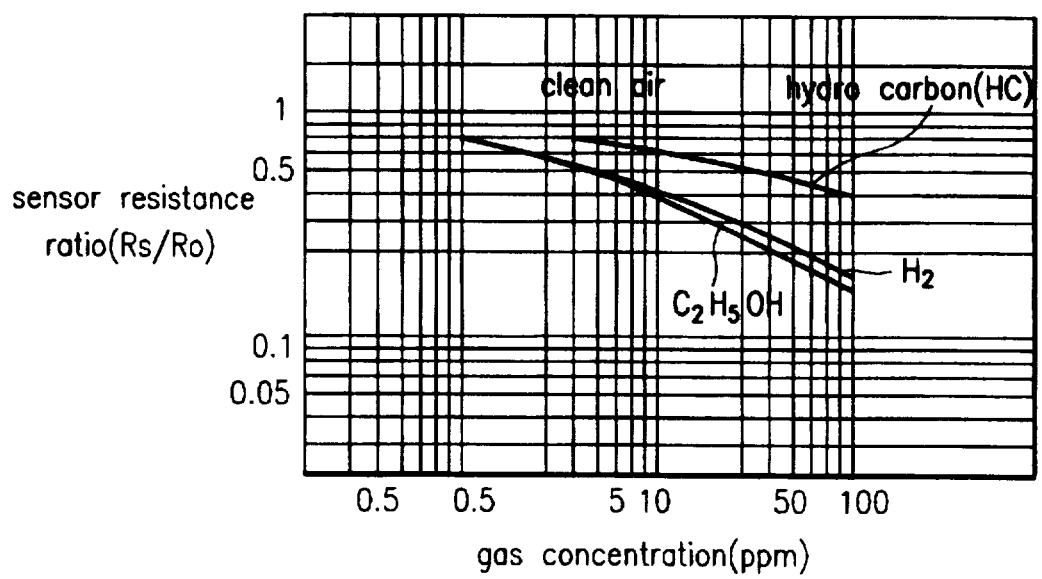
FIG. 2 shows gas detecting characteristics of a conventional air pollution gas sensor.
Figure 3:
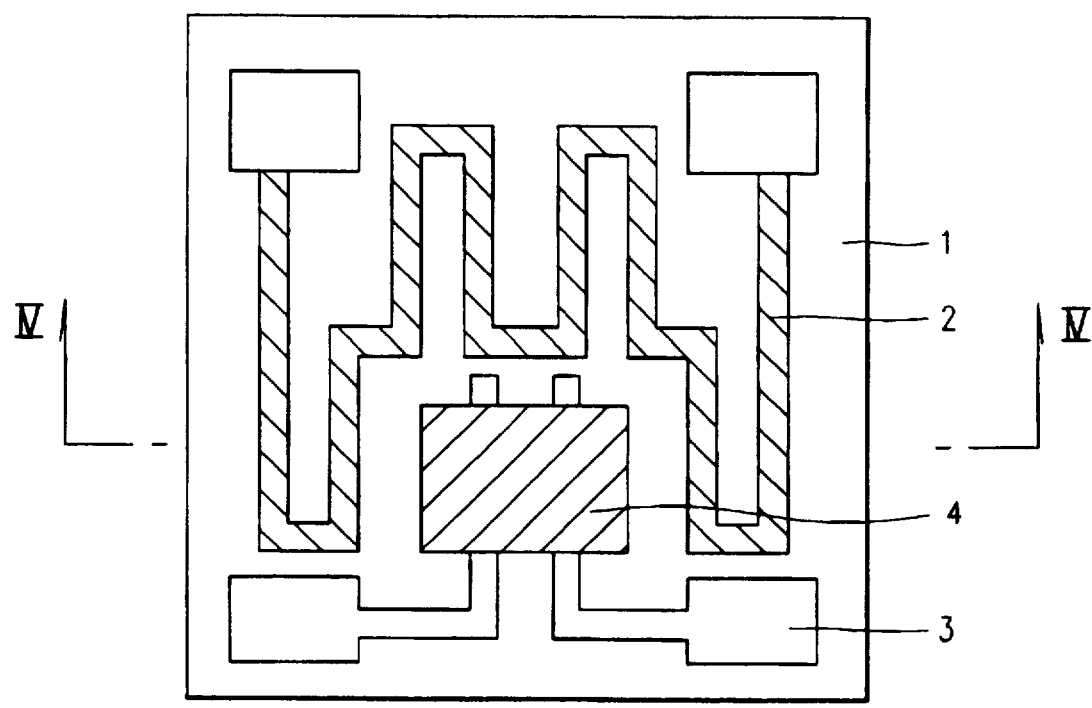
FIG. 3 is a layout of a air pollution gas sensor in accordance with the present invention.
Figure 4:
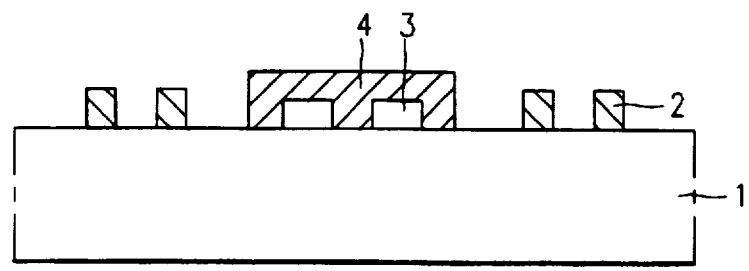
FIG. 4 is a sectional view of a air pollution gas sensor in accordance with the present invention.

FIG. 3 is a layout view in accordance with a air pollution gas sensor of the present invention and FIG. 4 is a sectional view across the line. IV—IV of Fig. Referring to FIG. 3, air pollution a gas sensor of the present invention includes a substrate 1 of $Al_2O_3$, a heater 2 of Pt formed on the $Al_2O_3$ substrate, and a sensing layer 4 of $SnO_2$ including $WO_3$ formed on the $Al_2O_3$ substrate 1 having electrodes 3 formed on the $Al_2O_3$ substrate, 1 and insulated from the heater 1.

A method for fabricating the air pollution gas sensor will be discussed below with reference to FIGS. 5a and 5b, which show the steps of processes for fabricating a air pollution gas sensor of the present invention.

Figure 5A:
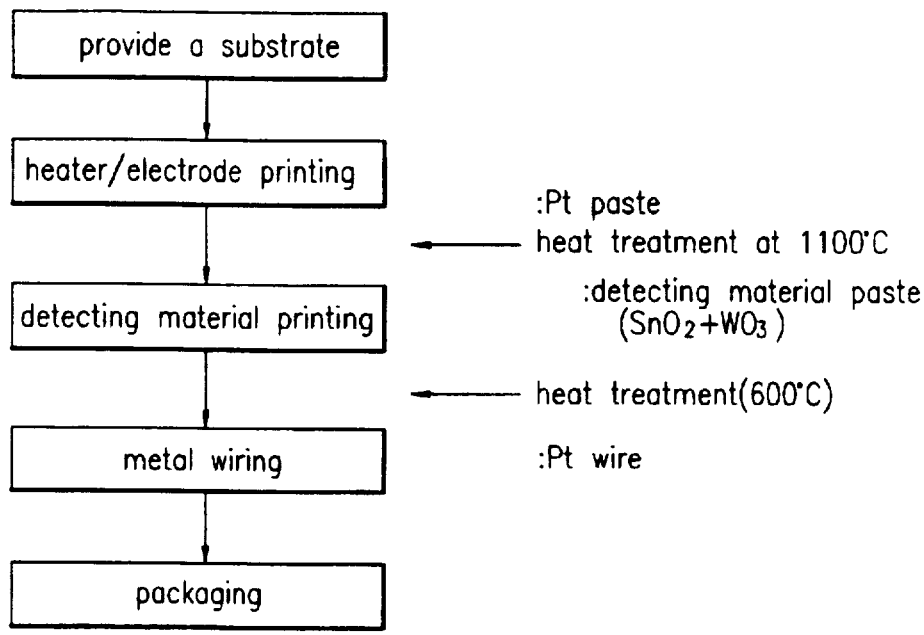
FIGS. 5a and 5b show steps of processes for fabricating a air pollution gas sensor in accordance with the present invention.
Figure 5B:
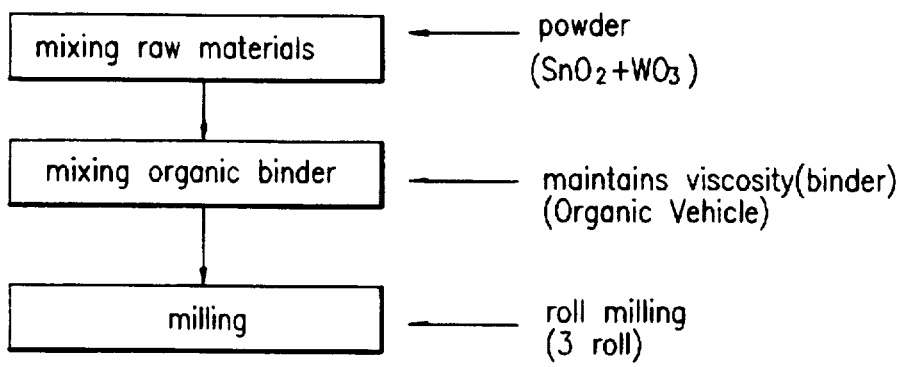

Referring to FIGS. 5a and 5b, in the method for fabricating air pollution a gas sensor of the present invention, a substrate of $Al_2O_3$ is first provided, a heater and a electrode pattern mask are formed to cover the $Al_2O_3$ substrate, and Pt paste is printed in the way of the screen printing on the $Al_2O_3$ substrate so that the heater 2 and the electrodes 3 are formed. The heater 2 and the electrodes 3 have to be insulated from each other. Then, after the substrate is dried, and subjected to heat treatment at a temperature about 1100° C. Then a sensing material paste is screen printed on the substrate of $Al_2O_3$ including the electrodes 3.

Referring, to FIG. 5b, in it the method for preparing the sensing material paste more than 90% of $SnO_2$ is mixed with 1–10% of $WO_3$, uniformly. Then an organic binder is added to uniformly mixed powder for paste of appropriate viscosity. Then the paste mixture is milled by a 3-roll mill so that the powder and organic binder are well-mixed, and milled to a predetermined size. As illustrated in FIG. 5a, the paste obtained thus is printed on the $Al_2O_3$ substrate 1 including the electrodes 3 in the way of screen printing to form the sensing layer 4. The substrate is dried for a predetermined period and subjected to heat treatment at a temperature of 600° C. Then even though it is not shown, Pt wires are connected to the heater 2 and the electrode 3, which is packaged to complete the gas sensor fabrication.

Figure 6:
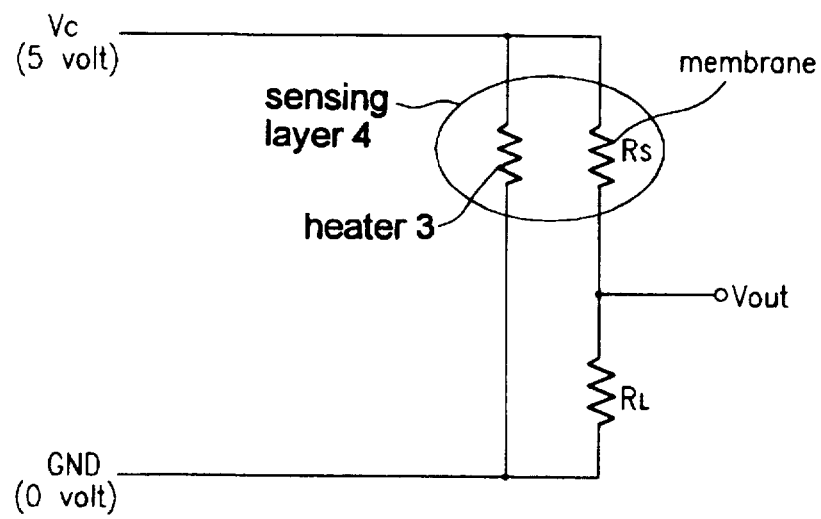
FIG. 6 illustrates a circuit for measuring a gas to which a air pollution gas sensor of the present invention is applied.

FIG. 6 is a circuit for operating the foregoing gas sensor. Referring to FIG. 6, the sensing layer 4 and the heater 3 are applied to a source of 5V which at the same time heat the air pollution gas sensor to a temperature of 250° C. and to connect a resistor $R_L$ to a resistor $R_s$ of the sensing layer 4 to have an output voltage.

When reducing gas is adsorbed on and makes a reaction with the surface of the air pollution gas sensor since the resistor $R_s$ of the sensing layer 4 decreases and the output voltage increases, the presence of the objective gas can be detected.

Figure 7:
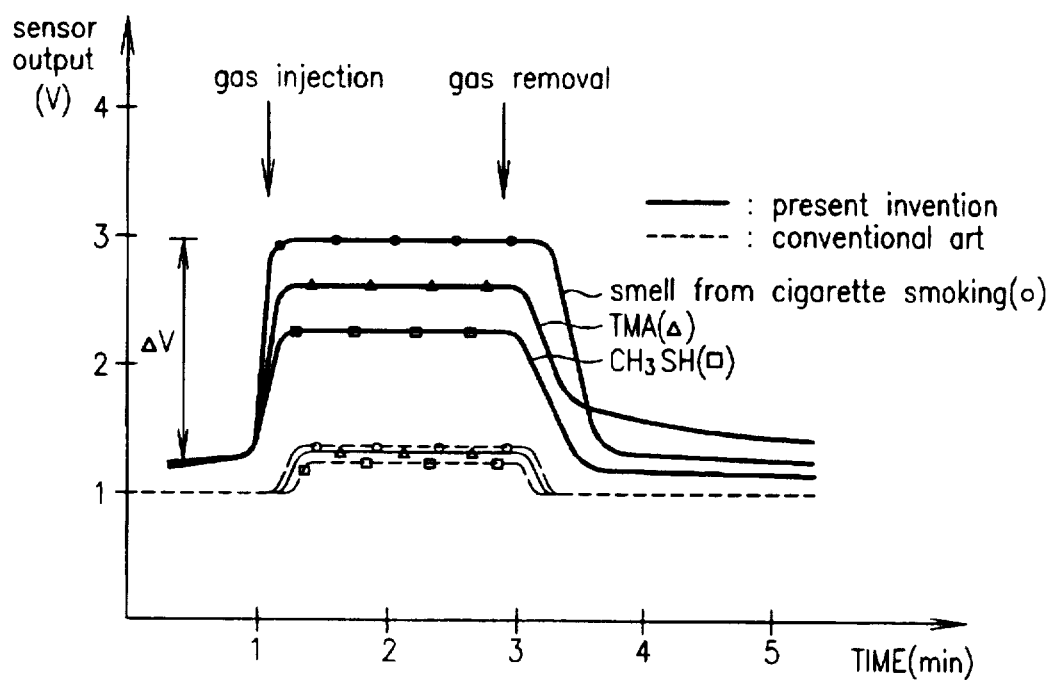
FIG. 7 shows the voltage output change characteristics of both a conventional air pollution gas sensor and a gas sensor of, the present invention.

FIG. 7 shows the output voltage characteristics of the conventional air pollution gas sensor and the air pollution gas sensor of the present invention for different typical constituents of smells. That is, FIG. 7 shows changes of output voltages of the air pollution gas sensor, as time goes by, in case a small gas is injected into a sealed, 50 (liter)1-volumed box which the air pollution gas sensor is installed.

Referring to FIG. 7, in case a small amount of cigarette smoke (an amount of smoke corresponding to an 1/20 piece of cigarette) is injected into the box, the air pollution gas sensor of the present invention is stabilized within about 30 seconds and shows an output voltage difference ($\Delta V$) more than 1.8V, when the conventional air pollution gas sensor merely shows 0.4V. The air pollution gas sensor of the present invention shows great changes of output voltage with respect to TMA and $CH_3SH$ which ingredients are known to be responsible for the characteristic stink of rotten food, Kimchi smell, and acetaldehyde, whereas the conventional air pollution gas sensor shows very low changes of output voltages. Accordingly, it can be known that the air pollution gas sensor of the present invention is very sensitive to the odorous presence of various rotten food.

The reason of such high sensitivity of the air pollution gas sensor of the present invention is that chemical reaction of a gas to be detected (i.e. TMA, CH3SH, Kimchi smell) occurs smoothly on the surface of the sensing layer 4 because a sensing material used as the sensing layer of the present invention is $SnO_2$ mixed well with the oxidating material catalyst, $WO_3$. The catalyst, $WO_3$, activates the reaction of organic gases on the surface of $SnO_2$ as shown in the below formula.

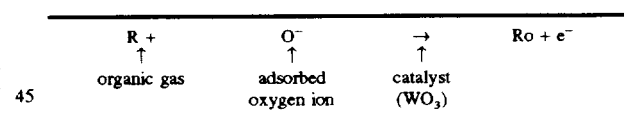

| R + | O⁻ | → | Ro + e⁻ |
|---|---|---|---|
| ↑ | ↑ | ↑ | |
| organic gas | adsorbed oxygen ion | catalyst ($WO_3$) | |

By the electron ($e^-$) generated as known in the above formula, an electrical conductivity, i.e., a resistance of the sensing layer is changed with change of output voltage of the air pollution gas sensor that indicates the presence of the objective gas of interest.

Besides, because the sensing layer of the air pollution gas sensor of the present invention is formed on the substrate in a plane form, the porosity of the sensing layer is easily controlled allowing formation of a greater contact area which makes for improvement of the sensitivity.

As described above, firstly, because the sensing layer is formed of $SnO_2$ with addition of a catalyzer, $WO_3$, the air pollution gas sensor of the present invention effectively detects tobacco smoke, TMA and $CH_3SH$ of rotten food smell, and acetaldehyde.

The plane form of the air pollution gas sensor of the present invention allows formation of a larger area of contact, which facilitates a better sensitivity to gas, simple structure, simple fabrication process that is favorable to mass production.

It will be apparent to those skilled in the art that various modifications and variations can be made in method for fabricating the air pollution gas sensor of the present invention without departing from the spirit or scope of the invention. Thus, it is intended that the present specification/ description cover the modifications and variations of this invention provided they come within the spirit and scope of the appended claims and their equivalents.

What is claimed is:

1. A gas sensor comprising:

a substrate;

a heater formed on said substrate;

electrodes each formed on said substrate electrically insulated from the heater; and, a sensing layer formed of $SnO_2$ including $WO_3$ added in a chemical mixture to be disposed on said substrate including said electrodes;

wherein a ratio of the mixture of $WO_3$ with respect to $SnO_2$ is between 1 and 10 wt %.

2. A method for fabricating a gas sensor comprising the steps of:

forming said heater on the substrate;

forming the electrodes on the substrate electrically insulated from the heater; and, forming a sensing layer of $SnO_2$ including $WO_3$ and an organic binder added in a chemical mixture to be disposed on the substrate including the electrodes;

wherein a ratio of the mixture of $WO_3$ with respect to $SnO_2$ is between 1 and 10 wt %.

3. A method for fabricating a gas sensor comprising the steps of:

forming said heater on the substrate;

forming the electrodes on the substrate electrically insulated from the heater; and, forming a sensing layer of $SnO_2$ including $WO_3$ and an organic binder added in a chemical mixture to be disposed on the substrate including the electrodes;

wherein preparing the sensing layer includes the steps of mixing $SnO_2$ with $WO_3$ uniformly to form a mixed powder, adding the organic binder to make the mixture achieve a proper viscosity, milling the mixture into a paste with 3-roll milling to attain a predetermined size of said powder and binder, and screen printing the paste on the substrate.

* * * * *